United States Patent [19]

Skoet et al.

[11] Patent Number: 4,687,742

[45] Date of Patent: Aug. 18, 1987

[54] **XYLOSE ISOMERASE (GLUCOSE ISOMERASE) FROM *STREPTOMYCES MURINUS* CLUSTER**

[75] Inventors: Georg Skoet, Virum; Hanne Guertler, Lyngby, both of Denmark

[73] Assignee: Novo Industri A/S, Bagsvaerd, Denmark

[21] Appl. No.: 715,936

[22] Filed: Mar. 25, 1985

[30] Foreign Application Priority Data

Mar. 12, 1985 [DK] Denmark .............................. 1111/85

[51] Int. Cl.$^4$ ..................... C12N 9/92; C12R 1/465; C12P 19/24
[52] U.S. Cl. .................................. 435/234; 435/94; 435/886
[58] Field of Search ................. 435/234, 233, 187, 94

[56] References Cited

U.S. PATENT DOCUMENTS

| | | | |
|---|---|---|---|
| Re. 29,152 | 3/1977 | Armbruster et al. | 435/233 X |
| 3,616,221 | 10/1971 | Takasaki et al. | 435/234 X |
| 3,622,463 | 11/1971 | Iizuka et al. | 435/234 X |
| 3,625,828 | 12/1971 | Brownwell | 435/234 |
| 3,989,596 | 11/1976 | Long | 435/187 X |
| 4,137,126 | 1/1979 | Weber | 435/234 |
| 4,351,903 | 9/1982 | Agudo et al. | 435/234 |
| 4,399,222 | 8/1983 | Bok et al. | 435/234 |
| 4,532,208 | 7/1985 | Hafner et al. | 435/94 |
| 4,551,430 | 11/1985 | Hafner | 435/94 |

*Primary Examiner*—Lionel M. Shapiro
*Attorney, Agent, or Firm*—Morris Fidelman; Franklin D. Wolffe

[57] ABSTRACT

Xylose isomerase, from strains of the *Streptomyces murinus* cluster, a method for production of such xylose isomerase, immobilized xylose isomerase and a method for isomerization of glucose to fructose therewith.

4 Claims, No Drawings

XYLOSE ISOMERASE (GLUCOSE ISOMERASE) FROM *STREPTOMYCES MURINUS* CLUSTER

This invention relates to a novel xylose isomerase, a method for production of such xylose isomerase, an immobilized xylose isomerase and a method for isomerization of glucose to fructose.

INTRODUCTION

All described glucose isomerases fundamentally are xylose isomerases. Also, in regard to enzyme nomenclature they are classified as EC 5.3.1.5, and glucose isomerase is not to be found in the official enzyme nomenclature. Thus, for the sake of clarity, the enzyme of this invention ordinarily will be identified as xylose isomerase, even though the most important application thereof is for the isomerization of glucose to fructose.

Enzymes capable of isomerizing glucose to fructose i.e., glucose isomerases, may be obtained from a large number of different microorganisms. Enzyme yield and the properties of the enzymes vary from species to species often from strain to strain. The growth medium is important. In all xylose isomerase producing strains found in nature, maximum enzyme production requires xylose in the growth medium.

BACKGROUND OF THE INVENTION

Syrups containing a mixture of glucose and fructose are widely used in industry for their sweet taste and their low tendency to crystallize. Such syrups are produced from glucose syrups using a xylose isomerase that exhibits glucose isomerase activity to catalyze isomerization of glucose to fructose. It is important for the economy of this enzymatic process that the enzyme costs be low and that there be a negligible formation of by-products requiring removal before the isomerized syrup can be used.

The production costs of microbially derived xylose isomerase depends largely on the cost of the fermentation substrate and the yield of enzyme from the cultivation. The most important enzyme characteristics for economic usefulness in the glucose isomeration process are enzyme purification yields and capability in the recovered enzyme to be converted to an immobilized enzyme product exhibiting satisfactory physical and enzyme chemical properties, including notably good stability at high temperatures, resistance towards physical pressure and a high half life.

No one of the xylose isomerases, heretofore known including, of course, the glucose isomerase products commercially heretofore employed are truly superior in all desired enzyme characteristics. The art has accepted compromise products.

As might be expected, a great amount of research has been carried out in efforts to discover a superior xylose isomerase from one microbiological source or another. This research is reflected in the patent literature. A large number of patents are directed to different microbial sources of xylose isomerase. Many bacteria, e.g., species belonging to the genera Streptomyces, Actinoplanes, Bacillus, and Flavobacterium, and fungi e.g., species belonging to the class Basidiomycetes, have been identified in the patent literature as xylose isomerase producing microorganisms. Also, just to choose some examples, from the bacterial genus of interest to this invention, namely, Streptomyces the following have been described in the patent literature as xylose isomerase producing microorganisms.

| U.S. Pat. No. 3,616,221 | |
|---|---|
| *S. flavovirens* | *S. albus* |
| *S. achromogenus* | *S. wedmorensis* |
| *S. echinatus* | |
| U.S. Pat. No. 3,622,463 | |
| *S. olivochromogenes* | *S. venezuelae* |
| U.S. Pat. No. 4,351,903 | |
| *S. griseoflavus* | |
| U.S. Pat. No. 4,137,126 | |
| *S. glaucescens* | |
| U.S. Pat. No. 3,625,828 | |
| *S. olivaceus* | |
| Hungary Patent No. 12,415 | |
| *S. galbus* | *S. niveus* |
| *S. gracilis* | *S. platensis* |
| *S. matensis* | |
| Germany Patent No. 2,417,642 | |
| *S. violaceoniger* | |
| U.S. Pat. No. 4,399,222 | |
| *S. acidodurans* | |
| Japan Patent No. 69,28,473 | |
| *S. phaeochromogenes* | *S. californicus* |
| *S. fradiae* | *S. vanaceus* |
| *S. rosechromogenes* | *S. virginiae* |
| *S. olivaceus* | |

Thus, the object of this invention is to provide a superior microbial xylose isomerase, namely, one which can be produced with an overall good compromise in regard to fermentation yield, purification yield and ability of the produced xylose isomerase to be converted to an immobilized product with satisfactory physical and enzyme chemical properties.

BRIEF STATEMENT OF THE INVENTION

Surprisingly, it has been found that microorganisms belonging to the *Streptomyces murinus* cluster are xylose isomerase producers in high fermentation yield and furthermore, that this xylose isomerase, an intracellular enzyme, can be produced with a good purification yield and an ability to be converted to an immobilized product with physical and enzyme chemical properties satisfactory for application in an industrial glucose isomerization process.

Moreover, constitutive strains of the *Streptomyces murinus* cluster provide special advantages in regard to fermentation economy.

Also, the invention comprises a method for production of a xylose isomerase, wherein an aerobic submerged fermentation is carried out with a strain of the *Streptomyces murinus* cluster on a conventional medium containing carbon and nitrogen, whereafter the thus formed xylose isomerase is recovered.

Also, the invention comprises an immobilized xylose isomerase characterized by the fact that the corresponding xylose isomerase is the xylose isomerase according to the invention. The immobilized product can be produced by means of several immobilization methods known per se, and it has been found that the immobilized xylose isomerase perform excellently in glucose isomerization columns. Reference is made to some of the following Examples.

Also, the invention comprises a method for isomerization of glucose to fructose, characterized by the fact that an aqueous solution of glucose is isomerized by means of a soluble preparation of the xylose isomerase produced according to the invention. In cases when a process utilizing a soluble xylose isomerase is preferred, the isomerization process proceeds satisfactorily.

Finally, the invention comprises a method for isomerization of glucose to fructose, characterized by the fact that an aqueous solution of glucose is isomerized by means of the immobilized xylose isomerase according to the invention. It has been found that a continuous glucose isomerization can be carried out on an industrial scale with superior economy and operational stability.

DETAILED DESCRIPTION OF THE INVENTION

To repeat, this invention relates to the xylose isomerase elaborated by strains of the *Streptomyces murinus* cluster.

The designation *Streptomyces murinus* cluster is to be understood as defined in Rolf-Dieter HEITZER's dissertation "Numerische Taxonomie der Actinomyceten-Gattungen STREPTOMYCES und STREPTOVERTICILLIUM" (filed Jan. 27, 1981), obtainable from Biological Department of the Technical University of Darmstadt, Germany. This means that *Streptomyces murinus* DSM 40091, DSM 40240 (previously named *S. roseoluteus*), DSM 3252 and DSM 3253 all belong to this *Streptomyces murinus* cluster.

It has been found that the xylose isomerase produced variously by these above indicated four members of the cluster are immunologically identical as determined by tandem crossed immunoelectrophoresis with antibodies produced against the xylose isomerase produced by means of DSM 3252, this identity emphasizing the close taxonomic relationship between these individual members of the cluster.

Despite the fact that a huge number of species are known to the art as xylose isomerase producers, no strain of the *Streptomyces murinus* cluster has been reported to be xylose isomerase producer, and surprisingly, it has been found that all strains of the *Streptomyces murinus* cluster tested by the inventors hereof is very well suited for production of the xylose isomerase of this invention.

In a preferred embodiment of the method according to the invention, the strain of the *Streptomyces murinus* cluster is selected from the group consisting of DSM 40091, DSM 40240, or DSM 3252. DSM is Deutsche Sammlung von Mikroorganismen, Gottingen, Germany. If xylose is present in the growth medium, the fermentation yield of xylose isomerase is satisfactory, and also, a satisfactory immobilized xylose isomerase product can be produced.

In a preferred embodiment of the method according to the invention, the strain of the *Streptomyces murinus* cluster is constitutive in regard to xylose isomerase production. Then it is not necessary to incorporate xylose, an expensive substrate component in the growth medium; any inexpensive carbon source, e.g., glucose will do. Surprisingly, it has been found that it is possible to find constitutive mutants of the *Streptomyces murinus* cluster, *Streptomyces murinus* DSM 3253 being a constitutive mutant of *Streptomyces murinus* DSM 3252.

DSM 3253 produces more xylose isomerase in media with glucose than in media with xylose, vide Example 1. In the prior art, mutant strains of xylose isomerase producing Streptomyces species referred to as "constitutive" (U.S. Pat. No. 4,399,222, Example 3 and U.S. Pat. No. Re. 21,152, Table 3) all produced higher enzyme yields when cultivated in xylose containing media than in media without the xylose inducer.

In a preferred embodiment of the method according to the invention the strain of the *Streptomyces murinus* cluster is DSM 3253. It has been found that a very high yield can be obtained with this strain on a xylose free culture medium, reference being made to Examples 1–3.

For the sake of a better survey, reference is made to the following Table I which shows some key properties of the *Streptomyces murinus* strains referred to in this specification.

TABLE I

| DSM deposition No. | Special feature | Deposited by us | Induceable | Constitutive |
|---|---|---|---|---|
| 40091 | Type strain | | x | |
| 40240 | Previously designated *Streptomyces roseoluteus* | | x | |
| 3252 | Isolated from soil sample | x | x | |
| 3253 | Mutated for constitutiveness | x | | x |

From Table II Shown below, some important taxonomic characteristics of the four *Streptomyces murinus* cluster strains appear.

TABLE II

| Characteristics for differentiation of Streptomycetes. | | DSM 3252 | DSM 3253 | DSM 40091 | DSM 40240 |
|---|---|---|---|---|---|
| 1. Aerial mycelium, spore colour | | R/Gr | R/Gr | R/Gr | R/Gr |
| 2. Pigment-melanoic | | − | − | − | − |
| 3. Pigment-reverse side | | − | − | Y/R | Y/R |
| 4. Pigment-soluble | | − | − | − | Y |
| 5. Spore chain morphology | | S | S | S | S |
| 6. Spore surface | | Sm | Sm | Sm | Sm |
| 7. Sugar utilization: | | | | | |
| Arabinose | (1%) | + | − | − | − |
| Xylose | (1%) | + | + | + | + |
| Inositol | (1%) | − | − | − | − |
| Mannitol | (1%) | + | + | + | + |
| Rhamnose | (1%) | − | − | − | − |
| Raffinose | (1%) | − | − | − | + |
| Fructose | (1%) | nd | + | + | + |
| Sucrose | (1%) | nd | − | − | − |
| 8. Metabolization of organic acids | | | | | |
| Oxalate | (0.1%) | − | − | − | − |
| Malonate | (0.3%) | + | − | − | − |
| Lactate | (1.0%) | + | (+) | − | + |
| Citrate | | + | + | + | nd |
| Gluconate | | + | + | + | nd |
| 5-keto gluconate | (0.5%) | − | nd | − | − |
| Acetate | (0.1%) | nd | nd | − | + |
| Butyrate | (0.1%) | nd | nd | + | + |
| Succinate | (0.1%) | nd | nd | − | nd |
| Adipate | (0.1%) | nd | nd | − | − |
| Malate | | + | + | + | + |
| 9. Metabolism of aromatic compounds | | | | | |
| Quinic acid | | − | − | − | − |
| p-hydroxy benzoic acid | (0.1%) | + | − | − | nd |
| 10. Inhibitory substances | | | | | |
| Rose bengal | (0.01%) | nd | nd | + | − |
| Eosin y | (1.00%) | + | nd | + | + |
| Toluidine blue | (0.01%) | nd | nd | − | − |
| Thallium acetate | (0.01 mg/ml) | nd | nd | − | − |
| Tellurite | (0.10 mg/ml) | + | nd | − | + |
| Tetrazolium | (0.10 mg/ml) | nd | nd | − | − |
| p. Amino- | (50.0 mg/ml) | nd | nd | − | + |

TABLE II-continued

| Characteristics for differentiation of Streptomycetes. | | DSM 3252 | DSM 3253 | DSM 40091 | DSM 40240 |
|---|---|---|---|---|---|
| salicylate | | | | | |
| Selenite | (1.00 mg/ml) | + | nd | + | + |
| Na—Dodecylsulfate | (0.10 mg/ml) | − | nd | nd | − |
| Furan-2-carbon-acid hydracide | (0.01 mg/ml) | nd | nd | + | − |
| Arsenite | (0.10 mg/ml) | − | nd | − | − |
| Pyronine | (0.01%) | − | nd | − | − |
| Thionine | (0.01%) | − | nd | − | − |
| Thiocyanate | 50.0 mg/ml | − | nd | − | − |
| 11. Urease activity (2%) | | nd | nd | nd | nd |
| 12. Egg yolk reaction (50 ml/l) | | − | nd | − | − |
| 13. Hemolysis (70 ml/l) | | − | nd | nd | − |
| 14. Resistance to lysozyme (100 mg/l) | | − | nd | − | − |
| 15. Allantoin (0.2%) | | + | nd | − | − |
| 16. Decomposition of aesculine (0.1%) | | − | nd | + | + |
| 17. Hydrolysis of casein (0.5%) | | − | nd | − | − |
| 18. Sensitivity to antibiotics | | | | | |
| Cephaloridin (25 μg) | | + | nd | + | + |
| Carbenicillin (100 μg) | | + | nd | + | + |
| Nitrofurantoin (100 μg) | | + | nd | nd | nd |
| Gramaxin (30 μg) | | nd | nd | + | − |
| 19. Antibiotica activity | | | | | |
| G+: Corynebacterium bovis | | − | − | − | + |
| Staphylococcus aureus | | − | nd | − | + |
| Bacillus cereus | | − | − | + | + |
| G−: Escericia coli | | − | − | + | + |
| Pseudomonas fluorescens | | − | − | − | − |
| Fungi: Geotrichum candidum | | − | − | + | + |
| Candida albicans | | nd | nd | + | + |
| Mucor ramannianus | | nd | nd | + | + |
| 20. Growth at pH 9 | | − | − | − | − |
| 21. Resistance towards NaCl | | | | | |
| 7% | | + | + | + | + |
| 10% | | − | − | − | − |
| 22. Maximum growth temperature | | 45° C. | 45° C. | 45° C. | 37° C. |

The significance of the abbreviations used in table II is as follows:
+ = positive test
(+) = doubtful
− = negative test
nd = not determined
R = red
Gr = grey
Y = yellow
S = spirals
Sm = smooth For further details in regard to conduct of the tests for the characterization results given in the above Table II, reference is made to the DSM publication "Methoden zur Untersuchung von Streptomyceten und einigen anderen Actinomyceten" edited by Hans J. Kutzner, Reiner M. Kroppenstedt and Felicitas Korn-Wendisch.

By and large, the *Streptomyces murinus* cluster represent advantageous microorganism sources for a commercial glucose isomerase posing no unusual requirements for their cultivation. State-of-the-art culture media and submerged aerobic fermentation may be employed. In addition, good fermentation yields result. Moreover, state-of-the-art enzyme immobilization methods produce granulate xylose isomerase preparations with acceptably high unit activity. Thus, practice of this invention contemplates preparation of granular immobilized xylose isomerase products from the cell mass of the *Streptomyces murinus* strain, which products preferably exceed 75 glucose isomerase units per gram of the enzyme preparation.

Isomerization of glucose to fructose, particularly, through continuous flow passage of a glucose solution through a bed of the granular immobilized xylose isomerase product can be carried out with superior economy and operational stability. Such method is contemplated within the practice of this invention.

If desired, the xylose isomerase may be liberated from the microorganism cells through conventional techniques and a soluble enzyme produced. Thus, for example the microorganism cells may be lysed and the thus liberated enzyme taken up in the aqueous solution. Soluble form xylose isomerase from strains of the *Streptomyces murinus* cluster have been found to be capable of isomerizing glucose in solution and, accordingly, practice of this invention contemplates also conduct of glucose isomerization with soluble forms of the xylose isomerase.

Practice of this invention will be illustrated by the following Examples.

Examples 1–4 illustrate fermentation of the xylose isomerase; Examples 5 and 6 illustrate production of the immobilized xylose isomerase and Example 7 illustrates the application of the immobilized xylose isomerase.

EXAMPLE 1

Fermentation in shake flasks

In this example all four above indicated strains of the *Streptomyces murinus* cluster were cultivated to produce xylose isomerase. Each of the strains was grown for one day at 37° C. on agar slants of the following composition expressed as g per liter of distilled water.

| Peptone (Difco) | 6 |
|---|---|
| Pepticase (Humco) | 4 |
| Yeast extract | 3 |
| Glucose | 1 |
| Beef extract | 1.5 |
| Agar | 2.0 |
| pH | 7.3 |

5 ml of a suspension of cells from each strain were then transferred to 100 ml of production medium in 500 ml baffle-bottom Erlenmeyer flasks. The production media a and b (pH 7.2) consisted of the following components in the quantities indicated (expressed as grams per liter of tap water).

| a: Corn steep liquour | 60 |
|---|---|
| (NH$_4$)$_2$SO$_4$ | 5 |
| K$_2$HPO$_4$ | 1.5 |
| Pluronic | 0.3 |
| Xylose | 5 |
| b: Corn steep liquour | 60 |
| (NH$_4$)$_2$SO$_4$ | 5 |
| K$_2$HPO$_4$ | 1.5 |
| Pluronic | 0.3 |
| Glucose | 5 |

Xylose and glucose were autoclaved separately and added aseptically after cooling to room temperature. The inoculated flasks were incubated at 30° C. After 72 hours of incubation the culture broths were assayed for xylose isomerase activity.

The results obtained are shown in the following Table III.

TABLE III

| | Xylose isomerase production | |
|---|---|---|
| | Isomerase activity GINU/ml | |
| Strain | Medium a (0.5% xylose) | Medium b (0.5% glucose) |
| DSM 3252 | 2.2 | 0.3 |
| | 2.5 | 0.4 |
| DSM 3253 | 4.4 | 5.1 |
| | 4.7 | 5.4 |
| DSM 40091 | 1.0 | 0.1 |
| DSM 40240 | 2.8 | 0.3 |

One GINU is the amount of enzyme which isomerizes 1 μmol of glucose to fructose per minute. Prior to the isomerization the samples are pretreated with lysozyme (2 mg/ml) at 37° C. for 30 minutes and $Mg^{++}$ and $Co^{++}$ are added in amounts sufficient to generate concentrations of 0.1M and 0.002M, respectively. Isomerization takes place at 65° C. in a 0.25 M maleate buffer of pH 6.50 which contains 5% glucose, 0.05M $Mg^{++}$, 0.002M $Co^{++}$ and 0.05% $CHCl_3$. After 20 minutes the reaction is stopped by addition of 0.1M perchloric acid. The formed fructose is then determined by the cysteine-carbazole reaction (Lloyd et. al., Cereal Chemistry 49, 544 (1972)).

EXAMPLE 2

Fermentation in 1.5 l fermentors

In this example DSM 3252 and DSM 3253 were grown on agar slants as in example 1, but at 30° C. After incubation for one day the colonies were harvested and used for inoculation in 1.5 l fermentors. The fermentation medium in the fermentors comprised: Corn steep liquour (40 g/l), $(NH_4)_2SO_4$ (4.5 g/l) $K_2HPO_4$ (1.5 g/l), antifoam (Pluronic 0.33 ml/l) and either glucose (5 g/l) or xylose (5 g/l) added after sterilization. pH was adjusted to 7.0 with NaOH prior to sterilization. The fermentors were run at 30° C. with an agitation of 750 rpm and an air flow rate of 0.6 vol/vol per minute. After 3 days the following results were obtained; vide table IV

TABLE IV

| Strain | DSM 3252 | | DSM 3253 | |
|---|---|---|---|---|
| Carbohydrate | Glucose | Xylose | Glucose | Xylose |
| GINU/ml | 0.35 | 3.20 | 4.78 | 4.87 |

EXAMPLE 3

Fermentation in 1500 l fermentor

In this example DSM 3253 was grown on agar slants as in example 1, but at 30° C. After incubation for 2 days the colonies were transferred to a sterilized 300 l fermentor containing corn steep liquour (12 kg), glucose (sterilized separately, 1.5 kg) and antifoaming agent (Pluronic 50 ml). Prior to sterilization, pH was adjusted to 7.0 with sodium hydroxide. This fermentor was operated at 30° C. with an agitation of 200 rpm and an air flow rate of 200 l/min. After 25 hours, 150 l from this fermentor was inoculated into the 1500 l fermentor containing corn steep liquour (60 kg), ammonium sulphate (6.75 kg), potassium dihydrogen phosphate (2.25 kg) and antifoaming agent (Pluronic, 250 ml). pH was adjusted to 7.0 before sterilization at 121° C. for 60 minutes. Operational temperature, agitation and aeration were 30° C., 190 rpm and 1000 l/min., respectively. After 3 hours, 8 kg of glucose was added and from 10 hours onwards, glucose was continuously added at a rate of 0.5 kg hour.

87 hours after inoculation the fermentor contained 11.9 GINU/ml or totally 18 MGINU.

EXAMPLE 4

Comparative fermentations in shake flasks

This example comprises several fermentations, some belonging to the prior art, some belonging to the invention, all in shake flasks. The fermentations are carried out in different media, as indicated in table V. The fermentations were carried out for two days at 30° C. The percentage ratio between the yield on the glucose containing medium and the yield on the xylose containing medium appears in the columns designated "Percentage degree of constitutiveness". All yields are expressed as total GINU/ml, the values indicated in the table below being averages of 2-8 independent fermentations.

TABLE V

| | Yields (GINU/ml) and Degree of Constitutiveness | | | | | |
|---|---|---|---|---|---|---|
| | Media related to this specification, and corresponding constitutiveness | | | | | |
| | Media from example 1 in this application | | Percentage degree of constitutive | Media from example 1 in this application | | Percentage degree of constitutive |
| Strain | Medium b (0.5% glucose) Col. 1 | Medium a (0.5% xylose) Col. 2 | Col. 3 | Medium b' (1% glucose) Col. 4 | Medium a' (1% xylose) Col. 5 | Col. 6 |
| DSM 3252 | 0.40 | 2.91 | 14 | 0.28 | 3.86 | 7 |
| DSM 3253 | 3.93 | 3.88 | 101 | 4.63 | 5.92 | 78 |
| ATCC 21114 | 0.76 | 3.27 | 23 | 0.18 | 4.31 | 4 |
| ATCC 21713 | 1.01 | 3.11 | 33 | 1.70 | 4.42 | 38 |
| ATCC 21714 | 1.84 | 3.45 | 53 | 2.04 | 4.10 | 50 |
| ATCC 21715 | 0.92 | 3.48 | 26 | 1.90 | 4.25 | 45 |
| NRRL 11489 | 0.19 | 1.23 | 15 | 0.13 | 1.35 | 10 |
| NRRL 11494 | 0.53 | 2.72 | 19 | 0.63 | 2.98 | 21 |
| NRRL 11497 | 2.02 | 4.56 | 44 | 1.78 | 3.87 | 46 |
| NRRL 11498 | 1.87 | 3.75 | 50 | 1.65 | 3.93 | 42 |
| | Media related to U.S. Re 29.152, Table 3 and corresponding constitutiveness | | | | | |
| | Medium A | Medium B 2.2% xylose, | Medium B' 2.2% glucose, | Percentage degree of constitutiveness | | |
| Strain | 2% corn syrup solids 15DE Col. 7 | 1.2% corn syrup solids 15DE Col. 8 | 1.2% corn syrup solids 15DE Col. 9 | $\frac{A}{B} \times 100$ Col. 10 | $\frac{B'}{B} \times 100$ Col. 11 | |

TABLE V-continued

| | Yields (GINU/ml) and Degree of Constitutiveness | | | | |
|---|---|---|---|---|---|
| DSM 3252 | 0.32 | 6.36 | 0.44 | 5 | 7 |
| DSM 3253 | 1.87 | 4.63 | 4.60 | 40 | 99 |
| ATCC 21114 | 0.35 | 6.82 | 0.37 | 5 | 5 |
| ATCC 21713 | 0.82 | 6.95 | 0.49 | 12 | 7 |
| ATCC 21714 | 0.75 | 4.12 | 0.44 | 18 | 11 |
| ATCC 21715 | 0.82 | 7.67 | 0.51 | 11 | 7 |
| NRRL 11489 | | | | | |
| NRRL 11494 | | | | | |
| NRRL 11497 | | | | | |
| NRRL 11498 | | | | | |

| | Media related to U.S. 4.399.222, example 3, and corresponding constitutiveness | | |
|---|---|---|---|
| Strain | 1.0% glucose Col. 12 | 1.0% xylose Col. 13 | Percentage of constitutiveness Col.14 |
| DSM 3252 | 0.63 | 2.70 | 23 |
| DSM 3253 | 3.14 | 3.90 | 81 |
| ATCC 21114 | | | |
| ATCC 21713 | | | |
| ATCC 21714 | | | |
| ATCC 21715 | | | |
| NRRL 11489 | 0.16 | 1.88 | 9 |
| NRRL 11494 | 0.15 | 1.46 | 10 |
| NRRL 11497 | 0.71 | 1.28 | 56 |
| NRRL 11498 | 0.57 | 1.26 | 45 |

The medium b' in column 4 is identical to the medium b in column 1, except for the fact that b' contains 1% glucose instead of 0.5% glucose. The media a' and a are interrelated in the same manner.

The percentage degree of constitutiveness, as exemplified for DSM 3253, column 11, is calculated as the percentage ratio between the yields in GINU/ml on the glucose containing medium and the xylose containing medium, i.e.

$$\frac{4.60}{4.63} \times 100\% = 99\%$$

From column 3 in relation to DSM 3253 it appears that DSM 3253 produces more xylose isomerase in medium b with glucose than in medium a with xylose. None of the other strains listed shows this extraordinary feature. Also it appears from the table that the percentage degree of constitutiveness of the prior art "constitutive" strains is very low in comparison with the percentage degree of constitutiveness of the constitutive strain DSM 3253 used in the method according to the invention. The medium B' in column 9 is designed by us in order to obtain a more fair calculation of the percentage degree of constitutiveness.

EXAMPLE 5

This example describes the immobilization of xylose isomerase produced by DSM 3252. A culture broth produced as described in example 2 with xylose in the medium was centrifuged, and the supernatant was discarded. The bottom phase, containing the cells with xylose isomerase activity, was freeze dried.

6 g of freeze dried cells were dissolved in 150 g deionized water with 3 g spray dried egg albumen. The pH was adjusted from 5.90 to 7.55 and 2.75 ml of 50% glutaraldehyde solution was added in order to crosslink the proteins. The pH was maintained at 7.5 for 35 minutes and thereafter diluted with 250 g deionized water. The mixture was flocculated with 30 ml of Superfloc C8351, a cationic flocculant, and 4.5 ml of A130, an anionic flocculant. The flocs were collected by filtration and the filter cake was granulated and dried. The activity of the dried granulate was 78.8 glucose isomerase units/g, the activity unit being defined in NOVO document F-850399.

EXAMPLE 6

This example describes the immobilization of xylose isomerase produced by DSM 3253. A culture broth produced as described in example 2 with glucose in the medium was centrifuged, and the supernatant was discarded. The cell sludge was used directly for the immobilization experiment.

6 g of spray dried egg albumen was added to 100 g cell sludge with 8.9% of dry substance. The pH was adjusted to 7.5 after addition of deionized water to a total volume of 1200 ml. 4.6 ml of 50% glutaraldehyde was added, and the pH was maintained at 7.5 by addition of NaOH solution. 500 ml of deionized water was added after 1 hour and the mixture was flocculated with the same flocculants as described in Example 5. The flocs were recovered by filtration, granulated and dried. The activity of the dried granulate was 184.5 glucose isomerase units/g, the activity unit being defined in NOVO document F-850399.

EXAMPLE 7

This example describes the application of the immobilized glucose isomerase produced from DSM 3253. 11.7 g of the dried granulate produced in Example 6 was soaked in 200 ml 45% w/w glucose syrup, pH 7.5 for two hours. The enzyme particles were then transferred to a water jacketed column and a 45% w/w glucose syrup with 0.4 g $MgSO_4$, $7H_2O/l$ and 2 mM $NaHCO_3$ at pH 7.5 was continuously pumped through the column at room temperature. After 1 hour the column temperature was raised to 60° C. and the flow adjusted to obtain a 41–44.5% conversion to fructose. The activity increased during the first 137 hours of isomerization. The syrup flow after 137 hours was 0.88 g syrup dry substance per g enzyme per hour and the degree of conversion in the outlet syrup was 44.3%. The experiment was terminated after 328 hours, the final syrup flow being 1.03 g syrup dry substance per g enzyme per hour with a degree of conversion in the outlet syrup of 42.0%.

We claim:

1. A method for producing xylose isomerase which comprises cultivating aerobically in submerged fermentation a xylose isomerase producing strain of the *Streptomyces murinus* cluster, selected from the group consisting of DSM 40091, DSM 40240, DSM 3252, DSM 3253 and mutants or variants thereof, and thereafter recovering the thus formed xylose isomerase from the fermentation broth.

2. The process of claim 1 further comprising cultivating in a xylose free growth medium, the constitutive DSM 3253 or a mutant or variant thereof.

3. The process of claim 1 wherein the recovered xylose isomerase comprises the microorganism cells, the process further comprising converting the microorganism cells into an immobilized enzyme granulate of activity exceeding about 75 glucose isomerase units per gram.

4. An enzyme product comprising the xylose isomerase of the *Streptomyces murinus* cluster strain DSM 3252 in cell mass immobilized enzyme granulate form with a unit activity exceeding about 75 glucose isomerase per gram.

* * * * *